United States Patent [19] [11] Patent Number: 5,252,698
Bhardwaj et al. [45] Date of Patent: Oct. 12, 1993

[54] METAL ION PORPHYRIN-CONTAINING POLY(AZINE)

[75] Inventors: Tilak R. Bhardwaj, Chandigarh, India; Susanna C. Ventura, Mountain View; Subhash C. Narang, Redwood City, both of Calif.

[73] Assignee: SRI International, Menlo Park, Calif.

[21] Appl. No.: 960,487

[22] Filed: Oct. 9, 1992

[51] Int. Cl.$^5$ ............................................. C08G 10/02
[52] U.S. Cl. ................................... 528/230; 528/248; 528/253; 528/265; 528/266; 528/423; 540/145; 540/200; 540/201; 540/203; 540/302
[58] Field of Search ............... 528/230, 248, 253, 266, 528/265, 423; 540/145, 200, 201, 203, 302

[56] References Cited

U.S. PATENT DOCUMENTS

| | | | |
|---|---|---|---|
| 4,106,466 | 8/1978 | Tsuchida et al. | 542/433 |
| 4,604,241 | 8/1986 | Sakata et al. | 540/145 |
| 4,614,723 | 9/1986 | Schmidt et al. | 436/536 |
| 4,772,681 | 9/1988 | Fukuda et al. | 540/145 |
| 4,816,386 | 3/1989 | Gotoh et al. | 430/495 |
| 5,091,502 | 2/1992 | Narang et al. | 528/229 |
| 5,162,231 | 11/1992 | Cole et al. | 436/64 |

Primary Examiner—Samuel A. Acquah
Attorney, Agent, or Firm—Phillips, Moore, Lempio & Finley

[57] ABSTRACT

The present invention relates to porphyrin and metal ion-containing monomers and polymers. The monomers

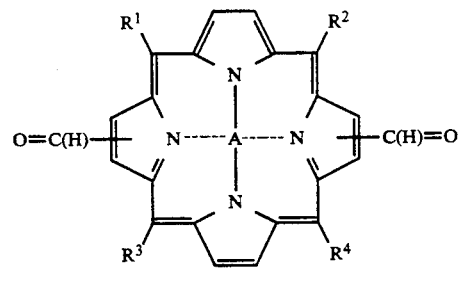

or

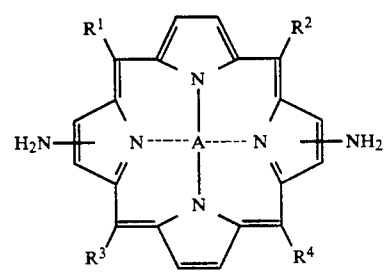

wherein $R^1$, $R^2$, $R^3$, and $R^4$ are independently selected from H, alkyl having 1 to 6 carbon atoms, phenyl or phenyl substituted with 1 to 3 alkyl groups each having 1 to 6 carbons or with 1 to 3 halogen atoms and A is a metal atom, are used with a diamine or a dialdehyde respectively to produce a porphyrin polymer or a metal ion containing porphyrin polymer. These polymers are useful as electrical conductors and as liquid crystal polymers.

20 Claims, 7 Drawing Sheets

FIG._1

PREPARATION OF 5, 10, 15, 20-
$R^1, R^2, R^3, R^4$ - PORPHYRIN

$R^1, R^2, R^3, R^4$ = PHENYL, et al

↓ ACETIC OR PROPIONIC ACID ($H_2$TPP)

PURIFICATION FROM CHLORIN BY REACTION WITH DDQ

DDQ =

β - PYRROLIC NITRATION

IIa

$N_2O_4$ or $I_2/AgNO_2$

IIIa

PREPARATION OF METALLO-PORPHYRIN POLYMERS

FIG._6

PREPARATION OF
METALLO-PORPHYRIN POLYMERS

I

1. COUPLING
2. TREATMENT WITH METAL SALT-A

FIG._7

PREPARATION OF METALLO-PORPHYRIN POLYMERS

METAL ION PORPHYRIN-CONTAINING POLY(AZINE)

BACKGROUND OF THE INVENTION

1. Field of Invention

The present invention relates to a porphyrin monomer, a porphyrin-containing poly(azine), and a metal ion porphyrin-containing poly(azine) and the process of formation thereof. More specifically, the invention relates to the preparation of specific porphyrin monomers having reactive diamine or dialdehyde substituents, their reaction with dialdehydes or diamines respectively, to produce polyporphyrin optionally containing one or more metal ions. The polymers are useful as semiconductors and electrically conducting films, nonlinear optical (NLO) materials, sensor materials, magnetic materials, electrochromic polymers, photo and electrocatalysts and advanced structural materials.

2. Description Of Related Art

There is a strong demand for the development of metal ion containing organic polymers for a variety of advanced electrical, optical and structural applications. To synthesize useful metal ion containing polymers is often a complicated time-consuming and costly process.

U.S. Patents of general interest include the following:

Tsuchida, et al. in U.S. Pat. No. 4,104,466 disclose non-azine polymeric metal ion complexes.

Fukuda, et al. in U.S. Pat. No. 4,772,681 disclose non-azine porphyrin derivatives for cancer diagnosis.

Schmidt, et al. in U.S. Pat. No. 4,614,723 disclose non metal ion-containing porphyrin monomer derivatives as immunoassay markers.

Gotoh, et al. in U.S. Pat. No. 4,816,386 disclose magnesium or aluminum ion-containing phthalocyanine monomer and polymer compositions.

S.C. Narang et al. in U.S. Pat. No. 5,091,502 disclose the synthesis of porphyrin-based metal ion-containing polymers using tetraketone porphyrin monomers and tetramines.

None of these references individually or collectively teach or suggest the present invention.

All references, articles, patents, standards and the like cited in this application are incorporated by reference in their entirety.

It is therefore desirable to produce new generation polymers which exhibit high thermal stability and good electrical conductivity without undue expense or time. The conjugated porphyrin based polymers of the present invention accomplish these objectives.

SUMMARY OF THE INVENTION

The present invention relates to a polyporphyrin-containing polymer of the structure:

or wherein $R^1$, $R^2$, $R^3$ and $R^4$ are each independently selected from alkyl having 1 to 6 carbon atoms, phenyl or phenyl substituted with 1 to 3 alkyl groups each having 1 to 6 carbon atoms or with 1 to 3 halogen atoms;

$R^5$ is independently selected from a direct bond, alkylene having 1 to 15 carbon atoms, alicyclic, alkylene alicyclic, aryl, substituted aryl, alkylenearyl, alkylene substituted aryl, or A in each porphyrin group is independently selected from two individual hydrogen groups or a metal atom;

B is independently selected from A; and n is an integer between 3 and 10,000.

The present invention also relates to a process to produce a polyporphyrin-containing polymer of the structure:

wherein $R^1$, $R^2$, $R^3$ and $R^4$ are each independently selected from H, alkyl having 1 to 6 carbon atoms, phenyl or phenyl substituted with alkyl groups having 1 to 6 carbon atoms or with 1 to 3 halogen atoms;

$R^5$ is independently selected from a direct bond, alkylene having 1 to 15 carbon atoms, alicyclic, alkylene alicyclic, aryl, substituted aryl, alkylenearyl, alkylene substituted aryl, or

A in each porphyrin group is independently selected from two individual hydrogen groups or a metal atom;

B is independently selected from A; and n is an integer between 3 and 10,000;

which process comprises:

(a) mixing 1 equivalent of wherein A, $R^1$, $R^2$, $R^3$ and $R^4$ are defined above with 1 or more equivalents of $O\!=\!C(H)\!-\!R^5\!-\!(C\!=\!O)H$ and $R^5$ is defined hereinabove, at between about 50° to 100° C. for between about 0.5 to 100 hr;

recovering the polyporphyrin-containing poly(azine) polymer; and optionally contacting the polymer with an aqueous metal salt; and optionally recovering the metal ion containing polyporphyrin poly(azine).

The present invention also relates to a process to produce a polyporphyrin-containing polymer of the structure:

wherein $R^1$, $R^2$, $R^3$ and $R^4$ are each independently selected from H, alkyl having 1 to 6 carbon atoms, phenyl or phenyl substituted with alkyl groups having 1 to 6 carbon atoms or with 1 to 3 halogen atoms;

$R^5$ is independently selected from a direct bond, alkylene having 1 to 15 carbon atoms, alicyclic, alkylene alicyclic, aryl, substituted aryl, alkylenearyl, alkylene substituted aryl, or

A in each porphyrin group is independently selected from two individual hydrogen groups or a metal atom;

B is independently selected from A; and n is an integer between 3 and 10,000;

which process comprises:

(a) mixing 1 equivalent of wherein A, $R^1$, $R^2$, $R^3$ and $R^4$ are defined above with 1 or more equivalents of $H_2N\!-\!R^5\!-\!NH_2$ and $R^5$ is defined hereinabove, at between about 50° to 100° C. for between about 0.5 to 100 hr;

recovering the polyporphyrin-containing poly(azine) polymer; and optionally contacting the polymer with an aqueous metal salt; and optionally recovering the metal ion containing polyporphyrin poly(azine).

The present invention also relates to the following porphyrin monomers wherein A, B, $R^1$, $R^2$, $R^3$, and $R^4$ are defined herein above:

or

-continued

BRIEF DESCRIPTION OF THE FIGURES

FIG. shows a reaction for the synthesis and purification the starting material 5,10,15,20 tetraphenylporphyrin (II).

DETAILED DESCRIPTION OF THE INVENTION AND PREFERRED EMBODIMENTS

Definitions

"Diamine structures" which are used in the present invention refer to, for example, the following known or commercially available structures found in Table 1 below:

TABLE 1

| Name | DIAMINES Structure |
|---|---|
| Aromatic diamines m- and p-phenylenediamine | (m- and p- phenylenediamine structures) |
| 2,4- and 2,6-diaminotoluene | (2,4- and 2,6-diaminotoluene structures) |
| p- and m-xylylenediamine | (p- and m-xylylenediamine structures) |

TABLE 1-continued

| Name | DIAMINES Structure |
|---|---|
| 4,4'-diaminobiphenyl | $H_2N$—⬡—⬡—$NH_2$ |
| 4,4'-diaminodiphenyl ether | $H_2N$—⬡—O—⬡—$NH_2$ |
| 4,4'-diaminobenzophenone | $H_2N$—⬡—C(=O)—⬡—$NH_2$ |
| 4,4'-diaminophenyl sulfone | $H_2N$—⬡—$SO_2$—⬡—$NH_2$ |
| 4,4'-diaminodiphenyl sulfide | $H_2N$—⬡—S—⬡—$NH_2$ |
| 4,4'-diaminodiphenylmethane | $H_2N$—⬡—$CH_2$—⬡—$NH_2$ |
| 3,3'-dimethylbenzidene | (3,3'-dimethylbenzidene structure with $CH_3$ groups) |
| 4,4'-isopropylidenedianiline | $H_2N$—⬡—$C(CH_3)_2$—⬡—$NH_2$ |
| 1,4-bis(p-aminophenoxy)benzene | $H_2N$—⬡—O—⬡—O—⬡—$NH_2$ |
| 1,3-bis(p-aminophenoxy)benzene | $H_2N$—⬡—O—⬡—O—⬡—$NH_2$ |
| Aliphatic diamines hexa-, hepta-, nona-, and decamethylenediamines | $H_2N$—$(CH_2)_n$—$NH_2$ where n = 6, 7, 9, or 10 |
| 1,4-cylclohexanediamine | $H_2N$—⬡—$NH_2$ |
| bis(4-aminocyclohexyl)methane | $H_2N$—⬡—$CH_2$—⬡—$NH_2$ |

"Metal(s)" refers to any atom of the Periodic Table having the properties of a metal. These include preferably all transition metals, actinides and lanthanides. More preferably tin, silicon, germanium, copper, iron, cobalt, zinc, nickel or manganese are used. See Porphyrins and Metalloporphyrins by K. M. Smith Elsevier/North-Holland Biochemical Press 1976, which is incorporated herein by reference.

"Metal salt" refers to an organic or inorganic salt used to treat a dihydro-porphyrin structure to produce the corresponding metal porphyrin compound. Acetates and propionates are preferred.

A general description follows for the monomers or polymers.

Synthesis of the Porphyrin Monomers

Referring to FIGS. 1 to 7, is described the synthetic route to obtain a diaminoporphyrin monomer, Compound I, e.g., where R is phenyl.

Figure 1:
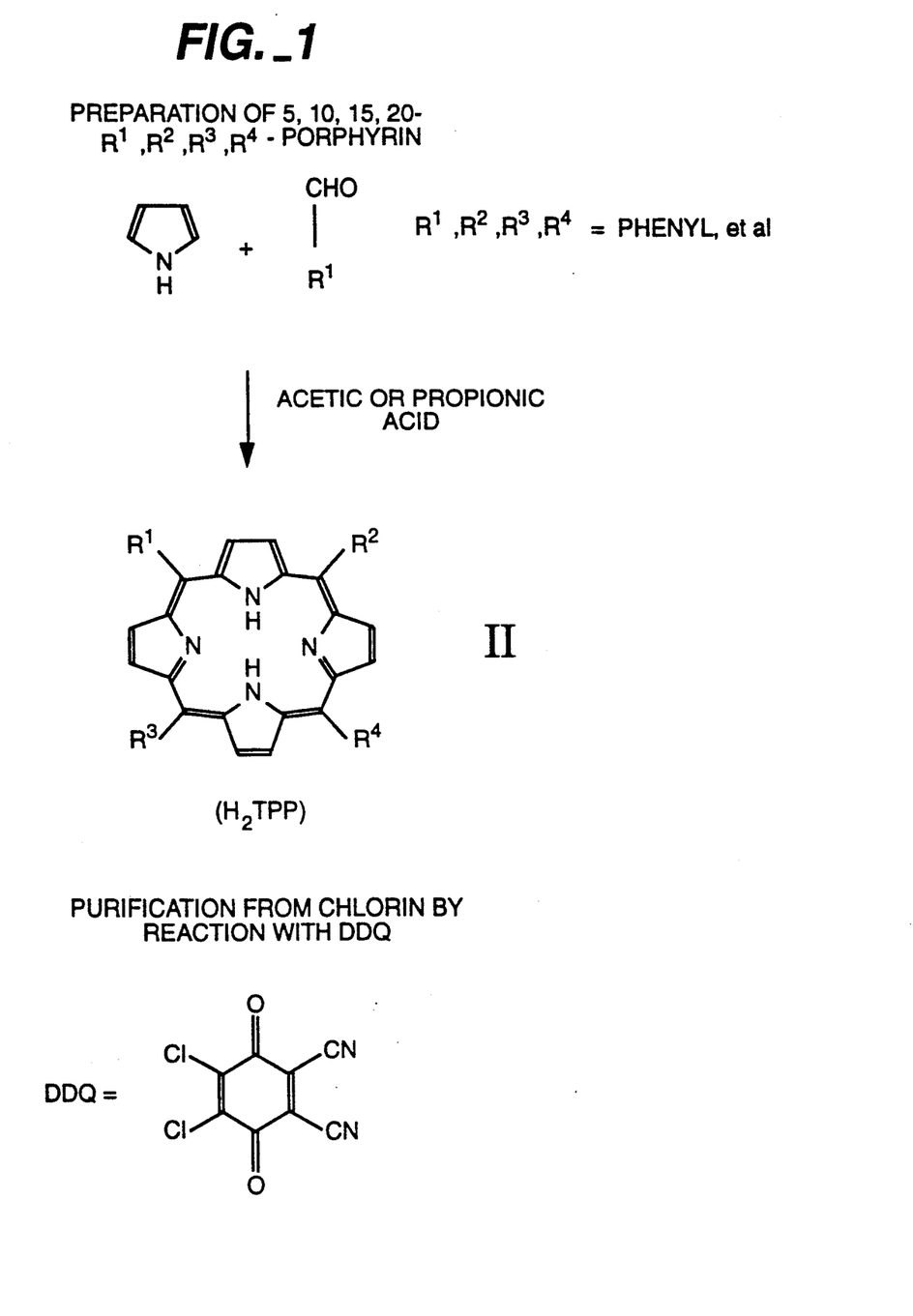
Figure 2:
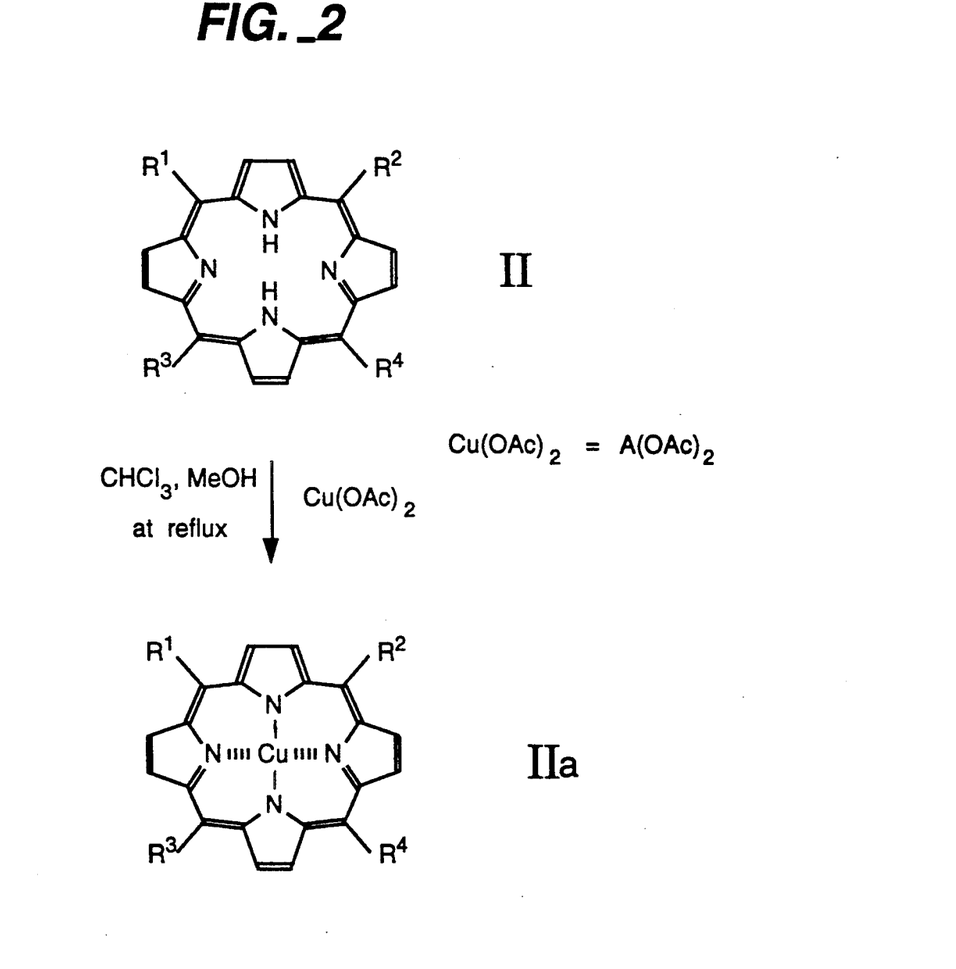
FIG. 2 shows a reaction for the synthesis of a copper (II) porphyrin intermediate.
Figure 3:
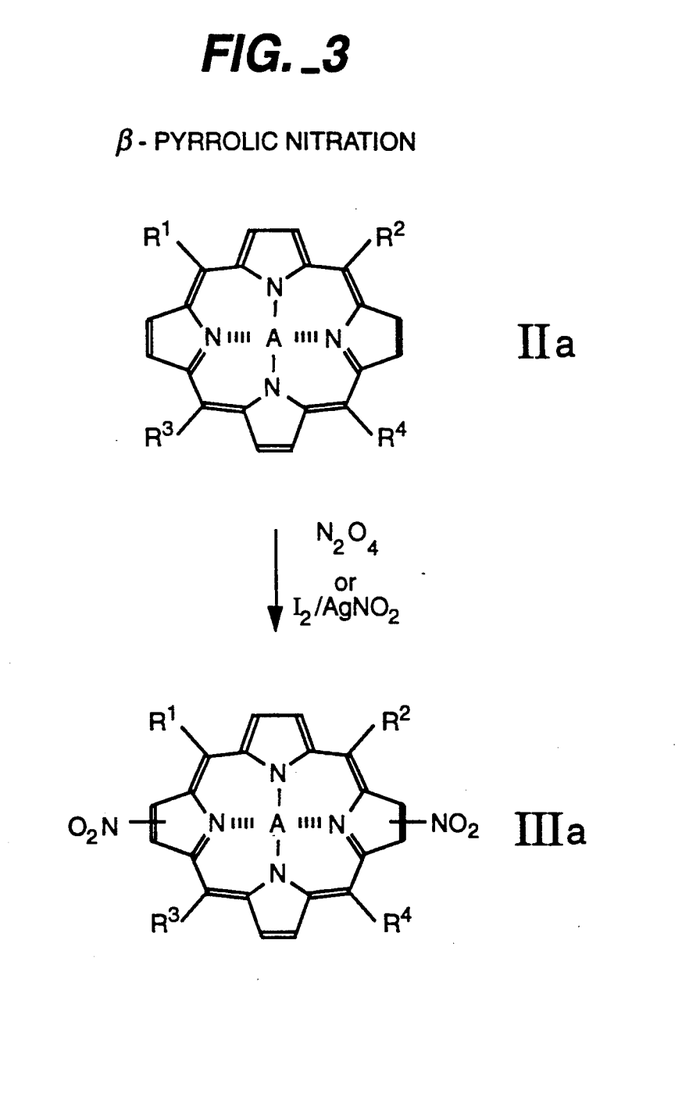
FIG. 3 shows a reaction for the synthesis of a dinitroporphyrin intermediate.
Figure 4:
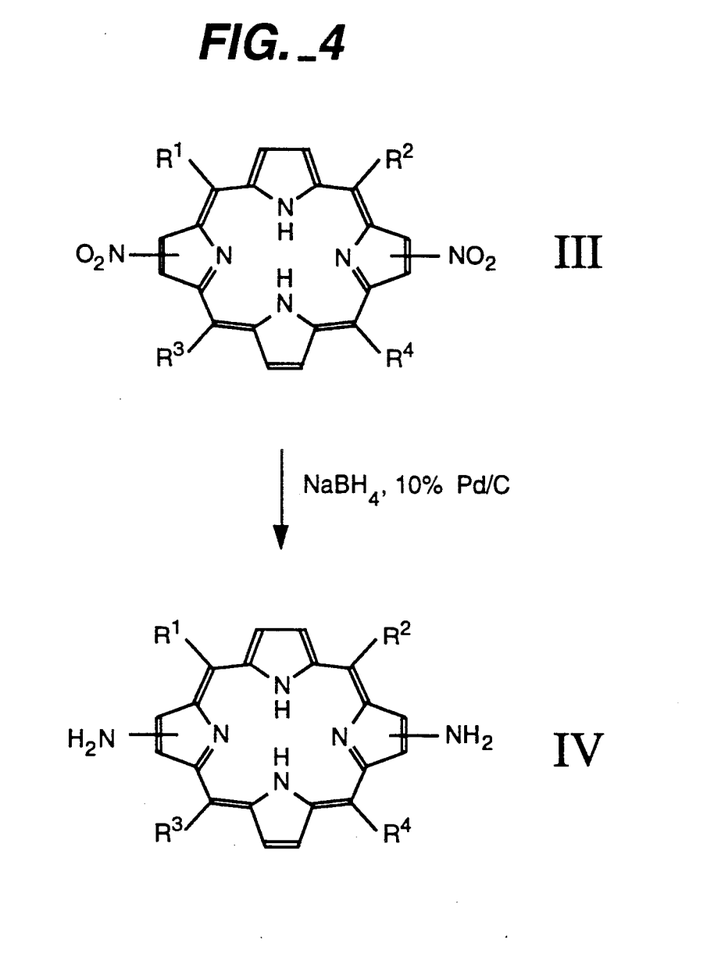
FIG. 4 shows a reaction sequence for the synthesis of a novel diaminoporphyrin (I), where $R^1$, $R^2$, $R^3$, and $R^4$ are each phenyl.
Figure 5:
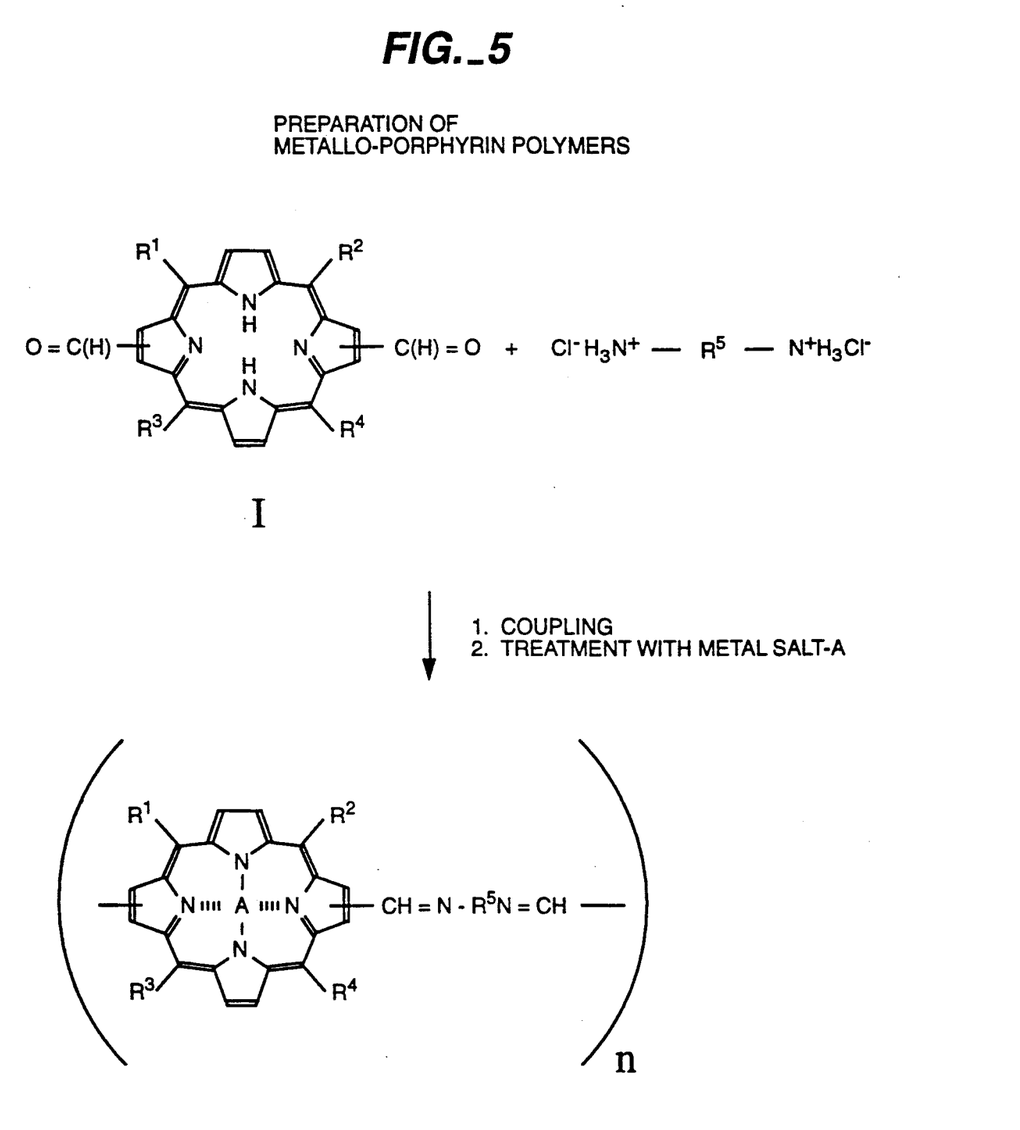
FIG. 5 shows a general reaction for the production of a linear metalloporphyrin polymer from porphyrin diamine and a dialdehyde, $(O=C)H—R^5—(C=O)H$ where $R^5$ is defined hereinabove.
Figure 6:
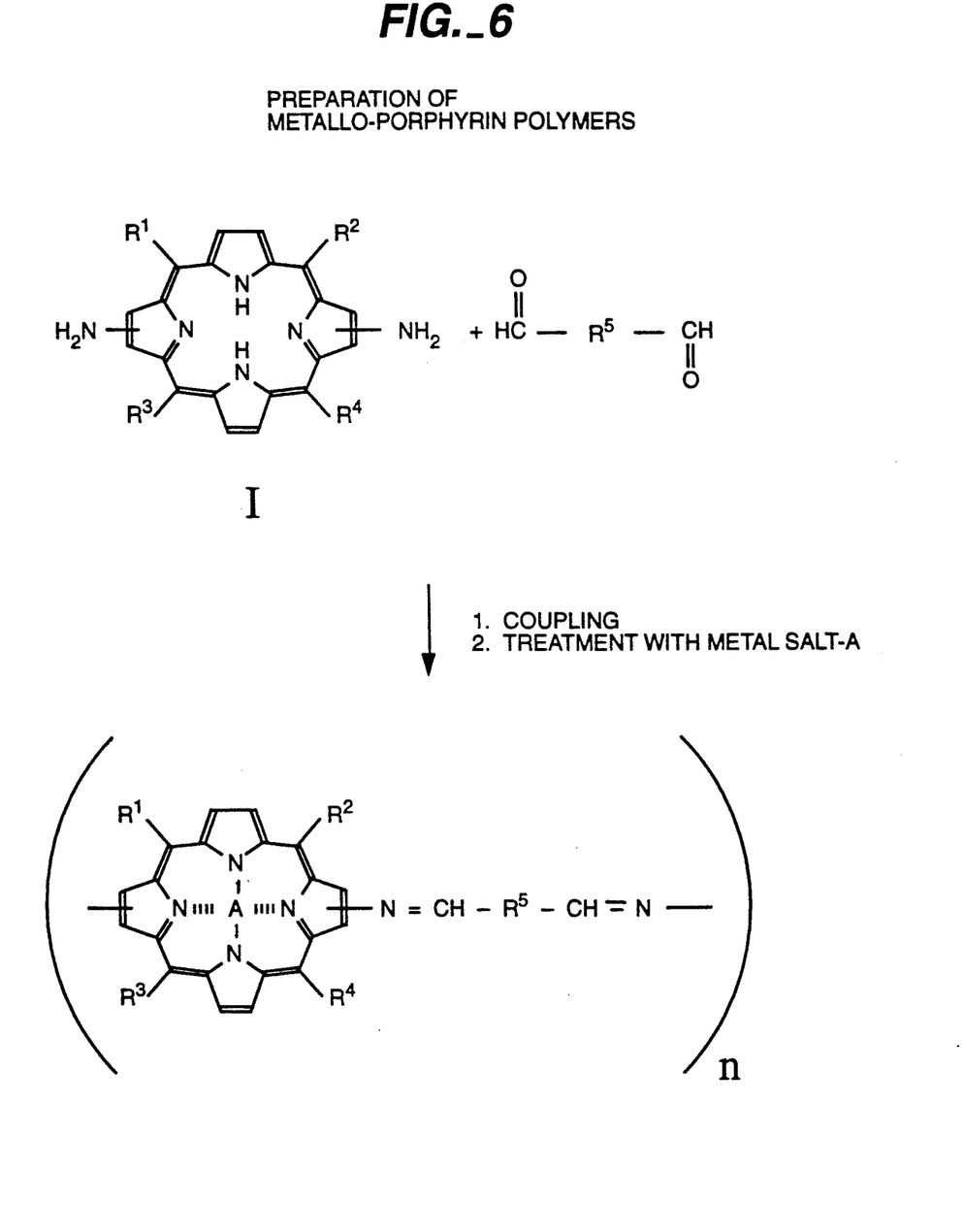
FIG. 6 shows a general reaction for the production of a linear metalloporphyrin polymer from porphyrin dialdehyde and a diamine, $H_2N—R^5—N—H_2$, where $R^5$ is defined hereinabove.
Figure 7:
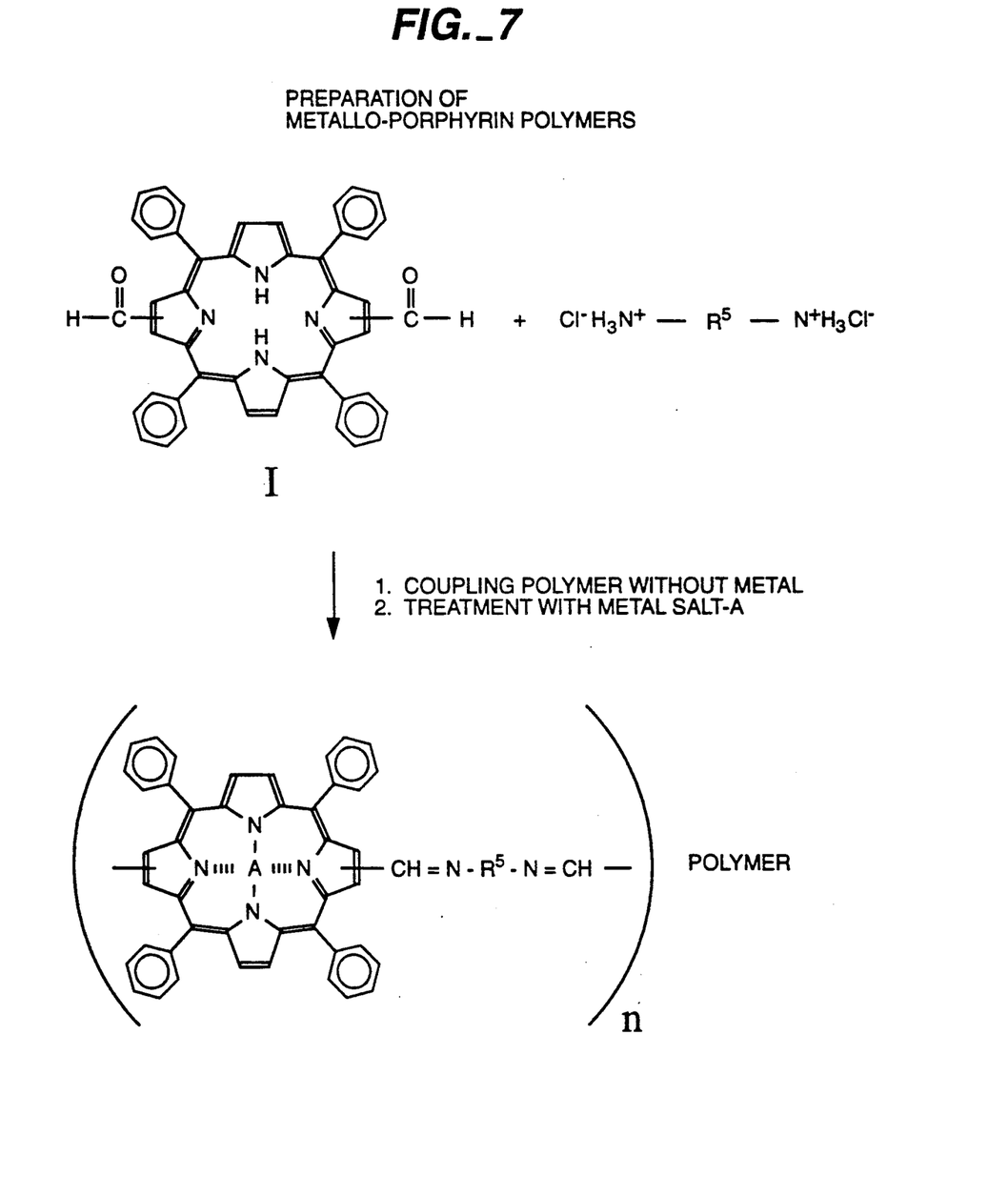
FIG. 7 shows a general reaction for the production of a linear metalloporphyrin polymer where $R^1$, $R^2$, $R^3$, and $R^4$ are each phenyl.

Tetraphenylporphyrin (Compound II): The preparation of Compound II is obtained according to the procedure reported by A. D. Adler, F. R. Longo, J. D. Finarelli, J. Goldmacher, J. Assour, and L. Korsakoff, *Journal of Organic Chemistry*, vol. 32, 476 (1967), which is incorporated herein by reference. Equimolar quantities of pyrrole and a benzaldehyde are combined using acetic acid or propionic acid.

Different porphyrin compounds are prepared by replacing the benzaldehyde with stoichiometrically equivalent amounts of 4-methylbenzaldehyde, 3,5-dimethylbenzaldehyde, 4-chlorobenzaldehyde, 4-methoxybenzaldehyde, acetaldehyde, propanaldehyde, cyclohexylaldehyde, and the like.

Metal Tetraphenyl Porhyrin (IIa): Compound II is combined with a metal acetate, in a solvent of, for example, chloroform and methanol. The solution is heated at reflux for between about 15 and 30 min. After cooling, the solid product IIa is obtained by filtration. Different metal acetate reagents will produce different metal porphyrins. Preferred metals include, for example, copper, iron, nickel, cobalt, or manganese. Copper is more preferred.

Metal (II) Dinitrotetraphenylporphyrins and their Demetallation: Compound IIIa: The metal (IIa) porphyrin, Compound IIa, is dissolved in excess aprotic solvent, such as methylene chloride, chloroform or the like, in an inert atmosphere, such as nitrogen or argon. Solvent and a nitrating agent, such as dinitrogen tetraoxide are combined. The nitrating agent solution is slowly added to the methylene chloride solution of the porphyrin. Next, the crude product is contacted with excess concentrated sulfuric acid. The product is carefully poured onto ice/water and extracted. The solid product is Compound III. The infrared, mass and proton nuclear magnetic spectral data are consistent with the dinitroderivative.

Diaminotetraphenylporphyrin-Compound IV: The dinitroporphyrin (Compound III) is dissolved in an aprotic solvent in an inert atmosphere. An alcohol, such as methanol, is added. A catalyst, such as palladium on carbon is added to the Compound III solution followed by a borohydride reducing agent, such as sodium borohydride. After filtration and removal of the solvent, the crude residue is purified by column chromatography using a polar solvent to produce diamino Compound IV.

Porphyrin-Monoaldehyde—Tetrasubstituted porphyrin also containing a metal (II) ion is contacted in an aprotic organic solvent, such as 1,2 dichloroethane and excess phosphorus oxychloride and dimethylformamide and the reaction is refluxed for 1 to 30 hr, preferably about 24 hr. The reaction mixture is cooled to ambient conditions, then stirred for to 6 hr with sodium acetate. The reaction product is extracted one or more times with a chlorinated hydrocarbon solvent such as dichloromethane or chloroform. The organic extracts are combined and washed with water or brine, dried and filtered. The product porphyrin monoaldehyde is obtained.

Porphyrin dialdehyde—The tetrasubstituted metal ion containing porphyrin monoaldehyde prepared above is further contacted with excess phosphorus oxychloride and dimethylformamide in a aprotic solvent such as 1,2 dichloroethane and refluxed in an anhydrous inert atmosphere for between about 6 to 48 hr, preferably about 24 hr. The reaction mixture is cooled to ambient conditions and stirred vigorously with a saturated aqueous sodium acetate solution for between 1 and 6 hr, preferably between about 2 and 3 hr. The crude product is extracted with a chlorinated hydrocarbon solvent such as dichloromethane, or chloroform. The organic extracts were combined and washed with water, and dried and filtered. A crude porphyrin dialdehyde was obtained after removal of the organic solvent under reduced pressure. The product can be further purified using chromatography, e.g. flash chromatography.

Formation of Linear Porphyrin Polymers

Compound I as the porphyrin dialdehyde or the porphyrin diamine is contacted with a diamine (or diamine hydrohalide) or a dialdehyde respectively, in the presence of a base and a dipolar aprotic solvent in the absence of light in an inert atmosphere. The polymer obtained is subjected to gel permeation chromatography to determine the mean molecular weight of the polymer. Usually a polymer having a molecular weight of about 20,000 daltons or greater (e.g. to about 2,000,000 daltons) is obtained.

These electrically conducting polymers are useful as liquid crystal polymers or initially, the polymers are evaluated by thermal gravimetric analysis (TGA) and differential scanning calorimetry (DSC). The rheological behavior is studied using a rheometrics mechanical spectrometer.

The electrical conductivity of the polymers is determined by the four-point probe method using cast films. The electrical conductivity ($\sigma$) was found for the iodine doped copper (II) polyporphyrin was between about 10 and $10 \times 10^{-5}$ ohm$^{-1}$cm$^{-1}$. The conductivity of polyporphyrin without metal was between about 1 and $1 \times 10^{-7}$ ohm$^{-1}$cm$^{-1}$. It is expected that these and the other polyporphyrin polymers described herein, including the described metal ions, will exhibit an electrical conductivity of between about $1 \times 10^{-4}$ to $10^{-6}$ ohm$^{-1}$cm$^{-1}$.

Changes in UV-visible spectra of the polymers with applied potential are determined by casting polymer films on indium-tin oxide (ITO), platinum or gold-coated semitransparent electrodes. Reversibility and response time are determined as is described in published methods. The following examples are provided to be illustrative and descriptive only. They are not to be construed as being limiting in any manner.

GENERAL—The materials and reagents used were obtained from standard chemical supply houses, e.g., Aldrich Chemical Company, Milwaukee, Wis. and were used without further purification, unless otherwise noted. Also see *Chemical Sources U.S.A.*, published annually by Directories Publications, Inc., Boca Raton, Fla. for starting materials and reagents.

EXAMPLE 1

Purification of Tetraphenylporphyrin 2,3-Dichloro-5,6-dicyano-1,4-benzoquinone (7.5 g) was dissolved in benzene (225.0 ml) and added slowly to the refluxing solution of commercially available tetraphenylporphyrin (30.0 g), Aldrich Chemical Co., Milwaukee, Wis. in ethanol-free chloroform (3.75-1). The reaction mixture was further refluxed under argon for 4-hr, cooled and filtered through a column packed with neutral alumina (500 g). The alumina was further washed with chloroform to recover the crude product as the filtrate. The filtrate was concentrated to about 200-ml using reduced pressure. The purified tetraphenylporphyrin, free from chlorin, was precipitated using methanol. The product was filtered using a vacuum and dried to obtain the pure dried product (26.0 g, 86.7% yield). See FIG. 1.

EXAMPLE 2

Copper (II) Tetraphenylporphyrin (a) A solution of tetraphenylporphyrin (26.0 g, $42.3 \times 10^{-3}$ mol) in chloroform (3.25 1) was refluxed under argon in a 5-1 three-necked, flask. To this reaction mixture was slowly added, a methanolic solution of copper (II) acetate (prepared by adding methanol (500 ml) to 14.0 g of copper acetate monohydrate). The sparingly soluble copper acetate was further dissolved repeatedly in 500-ml, 200-ml and 200-ml of methanol. The soluble portion was added very slowly to the refluxing solution. UV/VIS spectra and thin layer chromatography using prepared silica plates from Eastman-Kodak, Rochester, N.Y., using dichloromethane eluent, were used to monitor the progress of the reaction. The disappearance of the maxima at 512 $\mu$m and the appearance of another maxima at 538 $\mu$m (for Cu-porphyrin complex) was used to follow the progress and completion of the reaction (about 4-hr). The solvent was removed using reduced pressure to about 300-ml. The copper (II) porphyrin-complex was precipitated by the addition of excess methanol. The precipitated product was filtered using vacuum and dried under vacuum to yield the product: 26.5 g (92.9% yield). See FIG. 2.

(b) Similarly, when Example 2 (a) is repeated except that the copper (II) acetate is replaced by a stoichiometrically equivalent amount of nickel (II) acetate, iron(II) acetate, cobalt (II) acetate or manganese (II) acetate, the corresponding nickel (II), iron (II), cobalt (II), or manganese (II)-containing porphyrin is obtained in good yield.

EXAMPLE 3

Copper (II) Dinitrotraphenylporphyrin

In a 5-1 three-necked flask, copper (II) tetraphenylporphyrin (212, $31.0 \times 10^{-3}$ mol) was dissolved in dry dichloromethane (2.1-1), with stirring, under an argon blanket at ambient temperature. Freshly distilled nitrogen dioxide (4.0-ml) was condensed in a graduated cold finger, diluted with dry dichloromethane (8.0-ml), and transferred into 100-ml of dry dichloromethane in a graduated dropping funnel with the help of a needle transfer in an inert atmosphere. One-half of the solution was added dropwise slowly to the stirred solution of copper (II) tetraphenylporphyrin. Thin layer chromatography (Eastman Kodak silica plate, see above), dichloromethane/hexane; 6/4) performed after 15-min showed the formation of the mononitro complex and some starting material. The second half of the nitrogen dioxide solution was slowly added to the reaction mixture in small portions. Additional distilled nitrogen dioxide was condensed, diluted with dichloromethane (5.0-ml) and transferred into dichloromethane (50-ml) in a graduated dropping funnel. Again small portions of the new nitrogen dioxide solution was added slowly. Thin layer chromatography Eastman Kodak silica plate-dichloromethane as eluent was used to monitor the reaction and showed complete conversion of the mononitro complex to the dinitro complex. No spot was present in the TLC for the starting material. See FIG. 3.

EXAMPLE 4

Dinitrotetraphenylporphyrin

Copper (II) ion-containing dinitrotetraphenylporphyrin (24 g, $31.3 \times 10^{-3}$ mol) was dissolved in dichloromethane (500 ml) and stirred at ambient temperature in a 2-1 three-necked flask. To this solution was slowly and carefully added 96% sulfuric acid (100-ml), and then stirred for 30 min. The reaction product was carefully poured into ice cold water, and the aqueous solution was extracted with dichloromethane (3 $\times$ 100-ml). The organic extract was washed with water (3 $\times$ 100-ml), 5% aqueous sodium bicarbonate solution and dried using anhydrous sodium sulfate. The dried extract was separated by filtration, evaporated using reduced pressure and dried to product the crude subject compound, 20.9 g. This product showed no stretching band for C=O at 1720 cm$^{-1}$. The crude product was purified by passing through neutral alumina in dichloromethane to remove the base line. Purified product 19.9 g (90.1% yield) was obtained (without copper ion present). See FIG. 2, 3, and 4.

EXAMPLE 5

Diaminotetraphenylporphyrin

A 2-1 three-necked round bottomed flask was fitted with a condenser and a dropping funnel to add solid material. To this flask was added anhydrous dichloromethane (850-ml) and methanol (420-ml). To this organic solution was added 10% palladium on carbon (14.0 g), the mixture was stirred under an argon blanket, and then cooled in an ice bath. Sodium borohydride (4.0 g, mol) was added in small portions over about 30-min. Next the dinitrotetraphenylporphyrin (7.0 g, 0.01 mol) and solid sodium borohydride (14.0 g) were added in small portions over about 60-min. The reaction mixture was stirred under argon for 30 min. The reaction mixture was filtered through a layer of CELITE ® (diatomateous earth of Johns Manville, Denver, Colo.) in a Buchner funnel and washed repeatedly with dichloromethane. The solvent was completely removed under reduced pressure to produce a crude residue. The residue was redissolved in dry dichloromethane to separate insoluble CELITE ®, and filtered. The solvent was removed under reduced pressure and dried to produce a purified residue (6.2 g). This residue was flash chromatographed over silica using dichloromethane as eluent. The product obtained (0.6 g, 9.6% yield) was free of impurities. See FIG. 4.

EXAMPLE 6

Diaminotetraphenylporphyrin

Dinitrotetraphenylporphyrin (2.0 g 2.83 m mol) was added to a hydrogenation flask (500-ml) and dissolved in dry toluene (200-ml). To this solution was added the catalyst about 10% ruthenium on alumina pellets (4.0 g, from Engelhard Industries, Iselin, N.J.). After evacuation, and flushing with hydrogen, the reduction was performed at 70° at 60 psi for 8-hr. Next, the flask was cooled to ambient temperature, filtered in the dark to remove the catalyst. The solid catalyst was washed repeatedly with toluene to obtain the product. The organic solvent was removed under reduced pressure in the dark at 50° C. to produce the crude solid residue.

This residue showed one spot above the two spots near the base line for the product. An additional brown spot very close to the starting material was also observed. The residue was 1.6 g.

EXAMPLE 7

Polyporphyrin Poly(Azine) Polymer Formation

(a) Diaminotetraphenyl porphyrin (400 mg, 0.59 m mol), was dissolved in N, N-dimethylformamide (40-ml) and to this solution was added terephthaldicarboxyldialdehyde (85-mg, 0.63 mol). This reaction mixture was stirred and refluxed in the dark under argon for 4-days. The organic solvent was removed using reduced pressure to obtain the crude residue. The crude residue was stirred with methanol, filtered using reduced pressure and repeatedly washed with ethanol to produce the polymer (425 mg). Gel permeation chromatography of the product polymer showed that about 20% of the product as having a mean average molecular weight of about 2,000,000 daltons (92% yield). See FIG. 6.

(b) Similarly when the terephthaldicarboxylic dialdehyde is replaced by a stoichiometrically equivalent of a dialdehyde of the structure found in Table 2:

TABLE 2

DIALDEHYDES  O=CH—$R^5$—CH=O

TABLE 2-continued

DIALDEHYDES  O=CH—$R^5$—CH=O the corresponding polytetraporphyrin is obtained respectively.

EXAMPLE 8

Copper(II) Containing Polytetraphenylporphyrin Poly(Azine)

The polyporphyrin produced in Example 7(a) is then contacted with an aqueous copper acetate solution at ambient conditions for 2-4 hr. The copper containing polyporphyrin is obtained.

EXAMPLE 9

Tetraphenylporphyrin-Monoaldehyde

A solution of copper(II) tetraphenylporphyrin (1.25 g, $18.5 \times 10^{-4}$ mol), dimethylformamide (10-ml) and phosphorus oxychloride (10-ml) in 1,2-dichloroethane (200-ml) were refluxed for 24-hr. The reaction mixture was cooled and stirred further with saturated aqueous sodium acetate solution for 2 to 3 hr. The reaction product was extracted with chloroform (about 100 ml). The chloroform extract was then washed with water (about 100 ml), dried over anhydrous sodium sulfate, and filtered. The solvent was evaporated using reduced pressure to obtain a crude product (935 mg, 78%). The product was analyzed using thin layer chromatography Eastman Kodak silica with methylene chloride as eluent showing the porphyrin-monoaldehyde.

EXAMPLE 10

Tetraphenylporphyrin Dialdehyde

A mixture of copper(II) tetraphenylporphyrin monodialdehyde (935 mg), N,N-dimethylformamide (50-ml), phosphorus oxychloride (50-ml) and 1,2-dichloroethane (700-ml) was refluxed under an argon blanket for 24-hr. The reaction mixture was cooled to ambient temperature and stirred vigorously with a saturated aqueous sodium acetate solution for 2 to 3 hr. The crude product was extracted with chloroform (3 × 100 ml), the extract was washed with water, dried, filtered, and the solvent evaporated under reduced pressure to yield a crude residue. Thin layer chromatographic analysis (Eastman Kodak silica plate) of the residue (methylene chloride 100% as eluent) indicated 4 major spots (components), one blue having a minimum $R_f$ and the rest were all the same color, probably different isomers of copper(II)tetraphenylpolyporphyrin dialdehyde. (2.6 g,). This residue was further purified by flash chromatography using dichloromethane as eluent and silica gel (from Merck, Rahway, N.J.) an adsorbant. The following two fractions were obtained:

A: 190 mg blue colored isomer having a maximum $R_f$ m/e=731.

B: 950 mg - mixture of 3 spots $R_f$ lower than the F.I. blue colored isomer m/e=731.

Yield=1/16 g (21%) indicating and confirming different isomers of dialdehyde.

EXAMPLE 11

Porphyrin Dialdehyde and Diamine Copper(II)-Containing Tetraphenylporphyrin Poly(Azine)

(a) 1,4-Phenylenediamine (6.35 mg, $5.88 \times 10^{-5}$ mol) was added to a solution of copper (II) tetraphenylporphyrin dialdehyde (43 mg, $5.88 \times 10^{-5}$ mol from Example 10) in dry N,N-dimethylformamide (3-ml), and the reaction mixture was refluxed under argon for 7-days. Gel permeation chromatography of the reaction mixture indicated only insignificant conversion. Therefore, 2 to 3 g of activated molecular sieves (4 Angstrom) were added to the reaction mixture and it was refluxed under argon for 2.5 days. Gel permeation chromatography of an aliquot of the reaction mixture indicated that about 10 to 15 percent of polymerization to a molecular weight about 2,000,000 daltons. More molecular sieves (about 2 g) were added and the reaction mixture was further refluxed for 3 days. Gel permeation chromatography indicated not much improvement in molecular weight of the product. The reaction mixture was cooled, filtered and washed with N,N-dimethylformamide to yield the crude product. The solvent was removed using reduced pressure and the polymeric residue was dried. The product was further extracted/centrifuged with methanol followed by chloroform to yield purified polymer (40 mg 84% yield). Gel permeation chromatography of the purified polymer indicated that about 72% had a molecular weight of more than 100,000 daltons.

(b) Similarly when the procedure of subpart (a) is repeated except that 1,4-phenylenediamine is replaced by a stoichiometrically equivalent amount of any of the diamines found in Table 1 above the corresponding tetraphenylporphyrinpoly(azine) is obtained in good yield.

EXAMPLE 12

Porphyrin Diamine and Porphyrin Dialdehyde Copper(II)-Containing Tetraphenylporphyrin Poly(Azine)

(a) Diaminotetraphenylporphyrin (50 mg, 0.0775 mol) and copper(II)-containing tetraphenylporphyrin dialdehyde (57 mg, 0.085 mol) were dissolved in N,N-diamethylformamide (3.0-ml) and the reaction mixture was stirred and refluxed under an argon blanket. An aliquot of solution was removed after 4 days and analyzed by gel permeation chromatography which indicated some fraction of product had a high molecular weight of 2,000,000 daltons or higher. The reaction mixture was regularly monitored by gel permeation chromatography. After 64 days, the reaction was stopped, the solvent was evaporated under reduced pressure, and the crude residue was further dried under vacuum. This residue was washed with methanol followed by chloroform.

The chloroform and methanol insoluble residue (75 mg) indicated by gel permeation chromatography that more than 80% of the product had a molecular weight greater than 100,000 daltons. (Yield 72%).

EXAMPLE 13

Mixed Metal Ion Tetraphenylporphyrin Poly(Azine)

(a) The polyporphyrin poly(azine) of Example 12 (containing copper(II)) is further contacted with aqueous copper acetate solution.

(b) The polyporphyrin poly(azine) of Example 12 (containing copper (II)) is further contacted with aqueous nickel (II) acetate solution. The polymer containing copper (II) and nickel (II) ion is obtained in good yield.

EXAMPLE 14

Electrical Conductivity

The iodine-doped polyporphyrin of Example 7(a) (without metal ion) having a molecular weight of about 2,000,000 daltons is subjected to conventional electrical conductivity measurements A conductivity $\sigma = 9.28 \times 10^{-7}$ ohm$^{-1}$cm$^{-1}$.

EXAMPLE 15

Thermal Gravimetric Analysis (TGA)

The polyporphyrin of Example 7(a) is subjected to standard TGA condition in air. The decomposition temperature ($T_D$) is 405° C. (5% weight loss).

EXAMPLE 16

Electrical Conductivity

The iodine-doped copper (II) ion containing polyporphyrin of Example 12(a) having a molecular weight of about 2,000,000 daltons is subjected to conventional electrical conductivity measurements, showing a conductivity $(\sigma) = 2.56 \times 10^{-5}$ ohm$^{-1}$cm$^{-1}$.

While only a few embodiments of the invention have been shown and described herein, it will become apparent to those skilled in the art that various modifications and changes can be made in a metal ion porphyrin-containing poly(azine) and their method of manufacture without departing from the spirit and scope of the present invention. All such modifications and changes coming within the scope of the appended claims are intended to be carried out thereby.

What is claimed is:

1. A polyporphyrin-containing polymer of the structure:

or

-continued wherein $R^1$, $R^2$, $R^3$ and $R^4$ are each independently selected from H, alkyl having 1 to 6 carbon atoms, phenyl or phenyl substituted with 1 to 3 alkyl groups each having 1 to 6 carbon atoms or with 1 to 3 halogen atoms;

$R^5$ is independently selected from a direct bond, alkylene having 1 to 15 carbon atoms, alicyclic, alkylene alicyclic, aryl, substituted aryl, alkylenearyl, alkylene substituted aryl, or A is independently selected from two hydrogen groups or a metal atom;

B is independently selected from A; and n is an integer between 3 and 10,000.

2. The polyporphyrin-containing polymer of claim 1 wherein A and B are each independently selected from tin, silicon, germanium, iron, copper, cobalt, nickel, zinc or manganese.

3. The polyporphyrin-containing polymer of claim 1 wherein $R^1$, $R^2$, $R^3$ and $R^4$ are each phenyl.

4. The polyporphyrin-containing polymer of claim 1 wherein $R^5$ is selected from 1,4 phenylene or

5. The polyporphyrin-containing polymer of claim 4 wherein A and B are each independently selected from 2 hydrogen atoms, tin, silicon, iron, copper, cobalt, nickel or manganese.

6. The polyporphyrin-containing polymer of claim 1 wherein the metal atom is copper.

7. The polyporphyrin-containing polymer of claim 1 wherein $R^5$ is independently selected from $H_2N\!\!-\!\!(CH_2)_n\!\!-\!\!NH_2$
where n = 6, 7, 9, or 10, -continued 8. The porphyrin-containing polymer of claim wherein $R^5$ is and the average molecular weight of the polymer is between 10,000 and 2,000,000.

9. The porphyrin-containing polymer of claim 1 wherein the molecular weight of the polymer is between about 100,000 and 2,000,000 daltons.

10. The porphyrin-containing polymer of claim 1 wherein the electrical conductivity of the iodine-doped polymer is between about $1 \times 10^{-4}$ and $1 \times 10^{-5}$ ohm$^{-1}$ cm$^{-1}$.

11. The porphyrin-containing polymer of claim 3 wherein $R^5$ contains at least one aryl group.

12. The prophyrin-containing polymer of claim 11 wherein A and B are each independently selected from tin, silicon, germanium, iron, copper, cobalt, nickel, zinc or manganese.

13. A process to produce a polyporphyrin-containing polymer of the structure:

wherein
$R^1$, $R^2$, $R^3$ and $R^4$ are each independently selected from H, alkyl having 1 to 6 carbon atoms, phenyl or phenyl substituted with alkyl groups having 1 to 6 carbon atoms or with 1 to 3 halogen atoms;
$R^5$ is independently selected from a direct bond, alkylene having 1 to 15 carbon atoms, alicyclic, alkylene alicyclic, aryl, substituted aryl, alkylene, aryl, alkylene substituted aryl, or A is independently selected from two hydrogen groups or a metal atom.
B is independently selected from A; and
n is an integer between 3 and 10,000;
which process comprises:
(a) mixing 1 equivalent of wherein A, $R^1$, $R^2$, $R^3$ and $R^4$ are defined above with 1 or more equivalents of O=C(H)—$R^5$—(C=O)H and $R^5$ is defined hereinabove, at 50° to 100° C. for 0.5 to 1 hr;
and recovering the polyporphyrin-containing poly(azine) polymer.

14. The process of claim 1 wherein:
$R^5$ is independently selected from:
a direct bond;

where m is 1 to 15;

-continued

15. The product polymer of the process of claim 13 wherein the polymer is iodine-doped, and the conductivity is between about $1 \times 10^{-4}$ and $1 \times 10^{-5}$ ohm$^{-1}$ cm$^{-1}$.

16. A process to produce a polyporphyrin-containing polymer of the structure:

wherein

R$^1$, R$^2$, R$^3$ and R$^4$ are each independently selected from H, alkyl having 1 to 6 carbon atoms, phenyl or phenyl substituted with alkyl groups having 1 to 6 carbon atoms or with 1 to 3 halogen atoms;

R$^5$ is independently selected from a direct bond, alkylene having 1 to 15 carbon atoms, alicyclic, alkylene alicyclic, aryl, substituted aryl, alkylene, aryl, alkylene substituted aryl, or

A is independently selected from two hydrogen groups or a metal atom;

B is independently selected from A; and n is an integer between 3 and 10,000;

which process comprises:

(a) mixing 1 equivalent of wherein A, R$^1$, R$^2$, R$^3$ and R$^4$ are defined above with 1 or more equivalents of H$_2$N—R$^5$—NH$_2$ and R$^5$ is defined hereinabove, at 50° to 100° C. for 0.5 to 1 hr;

and recovering the polyporphyrin-containing poly(azine) polymer.

17. The process of claim 16 wherein H$_2$N—R$^5$—NH$_2$ is independently selected from:

-continued wherein a is 1 to 15;

18. A porphyrin monomer of either of the structures:

or wherein
R$^1$, R$^2$, R$^3$ and R$^4$ are each independently selected from H, alkyl having 1 to 6 carbon atoms, phenyl or phenyl substituted with 1 to 3 alkyl groups each having 1 to 6 carbon atoms or with 1 to 3 halogen atoms;
A is independently selected from two hydrogen groups or a metal atom.

19. The porphyrin monomer of claim 18 wherein R$^1$, R$^2$, R$^3$ and R$^4$ are each phenyl.

20. The porphyrin monomer of claim 19 wherein A is selected from tin, silicon, germanium, iron, copper, cobalt, nickel, zinc or manganese.

* * * * *